United States Patent [19]

Nakanishi et al.

[11] 4,444,885

[45] Apr. 24, 1984

[54] PROCESS FOR PRODUCING L-PROLINE BY FERMENTATION

[75] Inventors: Toshihide Nakanishi, Hofu; Hiroshi Hagino, Tokyo, both of Japan

[73] Assignee: Kyowa Hakko Kogyo Kabushiki Kaisha, Tokyo, Japan

[21] Appl. No.: 492,092

[22] Filed: May 6, 1983

Related U.S. Application Data

[63] Continuation of Ser. No. 270,433, Jun. 4, 1981, abandoned.

[30] Foreign Application Priority Data

Jun. 5, 1980 [JP] Japan ................................. 55-7492

[51] Int. Cl.$^3$ ......................................... ; C12P 13/24
[52] U.S. Cl. ..................................................... 435/107
[58] Field of Search ........................................ 435/107

[56] References Cited

U.S. PATENT DOCUMENTS

4,224,409  9/1980  Nakamori et al. .................. 435/107

OTHER PUBLICATIONS

Kato et al., Applied Microbiology, vol. 23, No. 4, pp. 758–764, Apr. 1972.
Derwent Abstract 62719T of Japanese Pat. No. 38196/1972.
Baich et al., Biochimica et Biophysica Acta, vol. 104, pp. 397–404 (1965).

*Primary Examiner*—Lionel M. Shapiro
*Attorney, Agent, or Firm*—Wolder, Gross & Yavner

[57] ABSTRACT

A process for producing L-proline by fermentation, comprising culturing a microorganism belonging to the genus selected from Corynebacterium, Arthrobacter, Brevibacterium, Microbacterium and Saccharomyces and capable of producing L-proline in a culture medium to accumulate L-proline in the cultured liquor and recovering L-proline therefrom, which process is characterized by the use of a culture medium containing at least one member selected from L-glutamic acid and D-, L- and DL-pyrrolidonecarboxylic acid in association with a carbon source, nitrogen source and inorganic compounds.

9 Claims, No Drawings

PROCESS FOR PRODUCING L-PROLINE BY FERMENTATION

This is a continuation of application Ser. No. 270,433 filed June 4, 1981, now abandoned.

FIELD OF THE INVENTION

This invention relates to a process for producing L-proline by using a microorganism. More particularly, this invention relates to a process for producing L-proline by culturing a microorganism belonging to the genus selected from Corynebacterium, Arthrobacter, Brevibacterium, Microbacterium and Saccharomyces and capable of producing L-proline in a culture medium to accumulate L-proline in the cultured liquor and recovering L-proline therefrom.

DESCRIPTION OF PRIOR ART

Various processes for the production of L-proline by fermentation are known. For example, L-proline is produced by culturing a wild strain, a nutrient-requiring strain or a strain being resistant to a certain chemical agent selected from the bacteria of the genera Brevibacterium, Microbacterium, Micrococcus, Paracolobacterium, Bacillus, Escherichia, Kurthia, Microbacterium and Corynebacterium or a yeast of the genus Saccharomyces [Japanese Patent Publications 11751/68, 13679/68, 1193/69, 1198/69, 6631/69, 26911/69, 38876/73, 28431/74, 33190/76, 40158/76, 41386/79 and 105293/79]. Further, the process characterized by adjusting the concentration of inorganic salts contained in the medium to a specified range is disclosed in Japanese Patent Publication Nos. 38557/71 and 42597/71. On the other hand, it is well known that the biosynthesis of L-proline is effected via L-glutamic acid and that the secretion of L-proline from a microorganism of *Escherichia coli* may be enhanced by addition of L-glutamic acid to the medium. However, the practical value of such a process is very small because the amount of the secreted L-proline is very low (e.g. about 0.03 g/l) [Biochimica et Biophysica Acta, Vol. 104, 397 (1965)].

It has also been reported that the production yield of L-proline by fermentation of *Kurthia catenaforma* may be improved by addition of a surfactant and L-glutamic acid to the culture medium [Applied Microbiology, vol. 23, 758–764 (1972)]. However, it has never been known that an increased amount of L-proline may be accumulated in the cultured liquor when the fermentation is effected by using a group of certain bacteria (the so-called glutamic acid-producing bacteria such as those belonging to the genera Corynebacterium, Brevibacterium, Arthrobacter, and Microbacterium in a medium to which L-glutamic acid is added [J. of the Japanese Agricultural Chem. Soc., vol. 42, 703–710 (1968); Amino Acids and Nucleic Acids, No. 16, 126–133 (1967)].

SUMMARY OF THE INVENTION

This invention is based upon the discovery that it is possible to improve the production yield of L-proline without addition of any surfactant to the medium when a microorganism selected from the bactria of the genera Corynebacterium, Brevibacterium, Arthrobacter, and Microbacterium and a yeast of the genus Saccharomyces are incubated in a culture medium containing at least one member selected from L-glutamic acid and L-, D- and DL-pyrrolidonecarboxylic acid.

An object of this invention is to provide a process for producing L-proline by fermentation. L-proline is widely used for example for the preparation of medicaments, foodstuffs and the like.

According to this invention, there is provided a process for producing L-proline by fermentation, comprising culturing a microorganism selected from a bacterium and yeast, capable of producing L-proline, in a culture medium to accumulate L-proline in the cultured liquor and recovering L-proline from the cultured liquor, characterized by using a culture medium which further contains at least one member selected from L-glutamic acid, and D-, L- and DL-pyrrolidonecarboxylic acid, in association with a carbon source, a nitrogen source and inorganic compounds.

The process of this invention will be fully and clearly described in the following specification.

The microorganisms which may be used for the purpose of this invention include L-proline producing microorganisms belonging to the genera Corynebacterium, Arthrobacter, Brevibacterium, Microbacterium and Saccharomyces, and the preferred strains are exemplified by

*Corynebacterium glutamicum* ATCC 21157
*C. glutamicum* ATCC 21158
*C. glutamicum* ATCC 21159
*C. glutamicum* ATCC 21355
*C. acetophilum* FERM-P 4045
*C. acetoacidophilum* FERM-P 4962
*Arthrobacter citreus* FERM-P 4963
*Brevibacterium lactofermentum* FERM-P 4964
*Microbacterium ammoniaphilum* FERM-P 4965
*Saccharomyces cerevisiae* ATCC 20169.

Either synthetic or organic medium may be used for the process of this invention, when the medium contains suitable amount of assimilable carbon source, nitrogen source, inorganic substances and other nutrients needed for the growth of the microorganism used. Preferred carbon sources are exemplified by carbohydrates such as glucose, fructose, sucrose, sorbitol, glycerol, maltose, mannitol, starch hydrolyzate, molasses and the like; organic acids such as acetic acid, pyruvic acid, lactic acid, fumaric acid, citric acid and the like; and alcohols such as e.g. methanol, ethanol etc. Preferred nitrogen sources are exemplified by ammonia; various inorganic and organic ammonium salts such as ammonium sulfate, ammonium chloride, ammonium phosphate, ammonium acetate and the like; various nitrogen-containing compounds such as urea and the like; peptone, meat extract, yeast extract, corn steep liquor, casein hydrolyzate, soybean meal hydrolyzate, fermented microbial bodies and hydrolyzate thereof. Examples of preferred inorganic substances include potassium dihydrogen phosphate, dipotassium hydrogen phosphate, magnesium sulfate, sodium chloride, ferrous sulfate, manganese sulfate, calcium carbonate and the like. In addition, traceable amounts of nutrients such as biotin, thiamine, pantothenic acid and the like may, if desired, be used. In the case of nutrient-requiring microorganism, it is necessary to add to the medium a suitable amount of such a nutrient required for the growth of the microorganism. Although such addition may not be needed if the required nutrient is inherently contained in the naturally-occuring substance used as the nitrogen source.

The sources of L-glutamic acid and L-, D- and DL-pyrrolidonecarboxylic acid which may be added to the culture medium are exemplified by isolated L-glutamic acid and sodium glutamate and L-, D- and DL-pyrrolidonecarboxylic acid; L-glutamic acid fermentation liquor such as glutamic acid fermentation broths, filtrate obtained by removal of microbial cells from the fermentation broths, mother liquor obtained by separating glutamic acid from the glutamic acid fermentation liquor, mother liquor obtained by separating sodium glutamate, beat molasses and waste liquor thereof containing a large amount of glutamic acid or pyrrolidonecarboxylic acid as well as other substances containing glutamic acid or pyrrolidonecarboxylic acid.

The amount of glutamic acid or pyrrolidone carboxylic acid contained in the medium may vary, depending upon the types of the used microorganisms and the time of addition of the acid and also upon the differing composition of the medium, and is usually more than 3 g/l of the medium. The upper limit may not be critical. However, at a concentration of more than 150 g/l, negative effects of the salt used for adjusting the pH as well as of the viscosity may be observed. The acid may be added to the medium at once or intermittently after the inoculation until the microorganisms grow stationarily. The conditions for proline fermentation may vary, depending upon the used microorganism, and the temperature is preferably within a range of 25° to 40° C. During the fermentation, the pH of the medium is preferably kept at 6–9 for example by using inorganic or organic substance having acidic or alkaline pH, urea, calcium carbonate and the like. Under these conditions, the fermentation is effected aerobically so as to accumulate a largest possible amount of L-proline, preferably for about 24–120 hours. The recovery of L-proline from the fermented broths may be effected by the known methods, such as the use of ion exchange resin, crystallization from methanol and the like, in combination.

PREFERRED EMBODIMENTS

The following non-limiting examples illustrate the invention, wherein the amount of proline was determined by the method reported in J. Biol. Chem., 199, 91–95 (1952).

EXAMPLE 1

A seed medium (30 ml) having the following composition was put in a 250 ml Erlenmeyer flask, sterilized and inoculated with *Corynebacterium acetophilum* FERM-P 4045. The fermentation was effected at 28° C. for 24 hours with shaking (220 r.p.m.):
Meat extract: 10 g/l, Peptone 10 g/l, Yeast extract: 3 g/l, Sodium chloride: 3 g/l (pH: 7.2).
The main medium had the following composition:
Waste molasses: 170 g/l (as glucose), Soybean meal hydrolyzate: 20 g/l, $KH_2PO_4$: 0.6 g/l, $MgSO_4.7H_2O$: 0.6 g/l, $(NH_4)_2SO_4$: 23.4 g/l, $FeSO_4.7H_2O$: 0.012 g/l, Thiamine hydrochloride: 100 μg/l, $CaCO_3$: 30 g/l, (pH=7.4).
To the main medium, a predetermined amount of sodium L-glutamate or DL-pyrrolidonecarboxylic acid as shown in Table 1 was added, and the medium (300 ml) was transferred to a 2 l Erlenmeyer flask equipped with a baffle on each occasion. After sterilization, each 30 ml of the said seed culture was inoculated to each main medium which was then cultured at 28° C. for 4 days with shaking (220 r.p.m.). On each occasion, the accumulated amount of L-proline is shown in Table 1.

TABLE 1

| Accumulated amount of L-proline by addition of (A) sodium glutamate or (B) DL-pyrrolidonecarboxylic acid (g/l of medium) | | |
|---|---|---|
| Added amount (g/l) | A (g/l) | B (g/l) |
| 0 | 25.1 | 24.8 |
| 1 | 25.3 | 25.1 |
| 3 | 26.9 | 27.7 |
| 10 | 31.4 | 30.1 |
| 20 | 35.6 | 34.8 |
| 50 | 39.1 | 35.4 |
| 90 | 40.5 | 36.6 |
| 100 | 40.7 | 36.8 |

EXAMPLE 2

*Arthrobacter citreus* FERM-P 4963, *Microbacterium ammoniaphilum* FERM-P 4965, *Brevibacterium lactofermentum* FERM-P 4964, and *Saccharomyces cerevisiae* ATCC 20169 were respectively treated by the method of Example 1 except the use of a main medium having the following composition:
Glucose: 100 g/l, $KH_2PO_4$: 0.5 g/l, $K_2HPO_4$: 0.5 g/l, $(NH_4)_2SO_4$: 30 g/l, Soybean meal hydrolyzate: 20 g/l, Biotin: 100 μg/l, $MgSO_4.7H_2O$: 0.25 g/l, $FeSO_4.7H_2O$: 12 mg/l, $MnSO_4.4H_2O$: 12 mg/l, $ZnSO_4.7H_2O$: 10 mg/l, Thiamine hydrochloride: 100 μg/l, $CaCO_3$: 30 g/l, (pH=7.2).
Before use, the main medium was added with sodium L-glutamate (20 g/l) or L-pyrrolidonecarboxylic acid (20 g/l) to accumulate L-proline as shown in Table 2.

TABLE 2

| Accumulated amount of L-proline by addition of (A) sodium glutamate or (B) L-pyrrolidonecarboxylic acid (g/l) | | | | | |
|---|---|---|---|---|---|
| (1) *Arthrobacter citreus* FERM-P 4963 | | | | | |
| (2) *Brevibacterium lactofermentum* FERM-P 4964 | | | | | |
| (3) *Microbacterium ammoniaphilum* FERM-P 4965 | | | | | |
| (4) *Saccharomyces cerevisiae* ATCC 20169 | | | | | |
| Additive | (g/l) | (1) | (2) | (3) | (4) |
| nil | — | 4.3 | 6.8 | 3.2 | 2.1 |
| A | 20 | 13.1 | 17.4 | 16.1 | 11.3 |
| B | 20 | 12.9 | 16.2 | 15.3 | 10.5 |

EXAMPLE 3

A similar treatment to that described in Example 1 was carried out by using *Corynebacterium glutamicum* ATCC 21355 and a medium having the following composition:
Glucose: 120 g/l, Urea: 3 g/l, Ammonium sulfate: 30 g/l, Ammonium chloride: 30 g/l, $KH_2PO_4$: 1.5 g/l, $K_2HPO_4$: 0.5 g/l, $MgSO_4.7H_2O$: 0.5 g/l, $FeSO_4.7H_2O$: 0.02 g/l, $MnSO_4.4H_2O$: 0.02 g/l, Biotin: 50 μg/l, Thiamine hydrochloride: 1 mg/l, Peptone: 10 g/l, (pH=7.2).
24 hours after the beginning of the fermentation, paraaldehyde (40 g/l) was added to the medium. The fermentation was effected at 28° C. for 4 days with shaking (220 r.p.m.) to accumulate 27.0 g/l of L-proline. A similar treatment effected with addition of 20 g/l of sodium glutamate gave 38.9 g/l of the accumulated L-proline.

EXAMPLE 4

A seed medium (200 ml) having the following composition was put in a 2 l Erlenmeyer flask equipped with a baffle and sterilized. After this, *Corynebacterium aceto-*

*philum* FERM-P 4045 or *C. acetoacidophilum* FERM-P 4962 was inoculated to the medium and cultured at 28° C. for 24 hours with shaking (220 r.p.m.).

Sucrose: 60 g/l, $KH_2PO_4$: 2 g/l, $MgSO_4.7H_2O$: 0.5 g/l, $FeSO_4.7H_2O$: 0.01 g/l, $MgSO_4.4H_2O$: 0.01 g/l, Corn steep liquor: 5 g/l, Thiamine hydrochloride: 100 μg/l, Biotin: 100 μg/l, Soybean meal hydrolyzate: 20 g/l, Urea: 3 g/l, (pH=7.4).

To a main medium having the following composition was added a mother liquor obtained by crystallizing and separating sodium glutamate in an amount of 20 g/l calculated as glutamic acid. Each 700 ml of the mixture was put in a 2 l jar fermentor and sterilized. After this, on each occasion, 200 ml of the seed culture was inoculated to the mixed main medium and cultured at 30° C. under aerobic condition. During the fermentation, the pH of the medium was adjusted to 7.0 by addition of acetic acid solution automatically.

Sucrose: 20 g/l, Ammonium acetate: 7 g/l, $MgSO_4.7H_2O$: 0.6 g/l, $KH_2PO_4$:4 g/l, $(NH_4)_2SO_4$: 40 g/l, Soybean meal hydrolyzate: 20 g/l, $FeSO_4.7H_2O$: 0.012 g/l, $MnSO_4.4H_2O$: 0.012 g/l, $ZnSO_4.7H_2O$: 0.01 g/l, Biotin: 100 μg/l, Thiamine hydrochloride: 100 μg/l, (pH=7.4).

72 hours after the beginning of fermentation, the consumed amount of acetic acid was 15% on the basis of the initial volume of the medium and the accumulated proline was 38.8 g/l by FERM P 4045 or 30.1 g/l by FERM-P 4962. For comparison, a similar treatment was carried out without addition of the glutamic acid solution and the corresponding value of proline was 25.4 g/l by FERM-P 4045 or 21.3 g/l by FERM-P 4962.

We claim:

1. A process for producing L-proline by fermentation, comprising culturing a microorganism selected from the group consisting of Corynebacterium, Arthrobacter, Microbacterium and Saccharomyces in a culture medium containing at least one member selected from D-, L- and DL-pyrrolidonecarboxylic acid to accumulate L-proline in the cultured liquor, and recovering L-proline therefrom.

2. The process of claim 1, in which the microorganism is selected from *Corynebacterium glutamicum, Corynebacterium acetophilum, Corynebacterium acetoacidophilum, Arthrobacter citreus, Microbacterium ammoniaphilum* and *Saccharomyces cervisiae.*

3. The process of claim 2, in which the microorganism is selected from the group consisting of *Corynebacterium glutamicum* ATCC 21157, *Corynebacterium glutamicum* ATCC 21158, *Corynebacterium glutamicum* ATCC 21159, *Corynebacterium glutamicum* ATCC 21355, *Corynebacterium acetophilum* FERM-P 4045, *Corynebacterium acetoacidophilum* FERM-P 4962, *Arthrobacter citreus* FERM-P 4963, *Microbacterium ammoniaphilum* FERM-P 4964 and *Saccharomyces cerevisiae* ATCC 20169.

4. The process of claim 1, in which the culturing is effected at a temperature of from 25° to 40° C. and at a pH of from 6 to 9.

5. The process of claim 1, in which at least one member selected from the group consisting of D-, L- and DL-pyrrolidone-caroboxylic acid is present in an amount of from 3 to 150 g/l of the medium.

6. A process for producing L-proline by fermentation, comprising culturing a microorganism selected from the group consisting of Corynebacterium, Arthrobacter, Microbacterium and Saccharomyces in a culture medium containing glutamic acid without addition of a surfactant to accumulate L-proline in the cultured liquor, and recovering L-proline therefrom.

7. The process of claim 6, in which the microorganism is selected from *Corynebacterium glutamicum, Corynebacterium acetophilum, Corynebacterium acetoacidophilum, Arthrobacter citreus, Microbacterium ammoniaphilum* and *Sacchromyces cerevisiae.*

8. The process of claim 7, in which the microorganism is selected from *Corynebacterium glutamicum* ATCC 21157, *Corynebacterium glutamicum* ATCC 21158, *Corynebacterium glutamicum* ATCC 21159, *Corynebacterium glutamicum* ATCC 21355, *Arthrobacter citreus* FERM-P 4963, *Microbacterium ammoniaphilum* FERM-P 4965 and *Saccharomyces cerevisiae* ATCC 20169.

9. The process of claim 6, in which the amount of glutamic acid is from 3 to 105 g/l of the medium.

* * * * *